US012765662B2

(12) United States Patent
Li

(10) Patent No.: US 12,765,662 B2
(45) Date of Patent: Oct. 20, 2026

(54) MODULAR LIQUID CONTAINER SYSTEM

(71) Applicant: Abamerica CORPORATION, San Diego, CA (US)

(72) Inventor: Hui Li, San Diego, CA (US)

( * ) Notice: Subject to any disclaimer, the term of this patent is extended or adjusted under 35 U.S.C. 154(b) by 0 days.

(21) Appl. No.: 19/458,595

(22) Filed: Jan. 23, 2026

(65) Prior Publication Data

US 2026/0150954 A1 Jun. 4, 2026

(51) Int. Cl.

| | |
|---|---|
| ***A45F 5/00*** | (2006.01) |
| ***A44C 25/00*** | (2006.01) |
| ***A45D 34/04*** | (2006.01) |
| ***A61L 9/12*** | (2006.01) |
| ***F16B 45/02*** | (2006.01) |

(52) U.S. Cl.

CPC .......... *A45F 5/1566* (2025.01); *A44C 25/007* (2013.01); *A45D 34/041* (2013.01); *A61L 9/12* (2013.01); *F16B 45/023* (2021.05); *F16B 45/024* (2021.05); *A45D 2200/057* (2013.01)

(58) Field of Classification Search

CPC .. A45D 34/02; A45D 34/041; A45D 40/0075; A45D 40/261; A45D 37/00; A45D 2034/002; A45D 2034/007; A45D 2040/0006; A45D 2040/0012; A45D 2200/057; A45F 5/1566; A44C 25/0107; A61L 9/12; B65D 47/04; B65D 51/245; B65D 2251/06

USPC .................................................... 401/88, 209

See application file for complete search history.

(56) References Cited

U.S. PATENT DOCUMENTS

| | | | | |
|---|---|---|---|---|
| 10,011,402 | B2 * | 7/2018 | Hui | B65D 47/04 |
| 11,882,914 | B2 * | 1/2024 | Miranda de Faria | A45D 34/041 |
| 2010/0102142 | A1 * | 4/2010 | Tagliareni | A61L 9/042 239/36 |
| 2022/0047046 | A1 * | 2/2022 | Mesica | A45D 34/04 |

FOREIGN PATENT DOCUMENTS

| | | | | | |
|---|---|---|---|---|---|
| CN | 205931651 | U | * | 2/2017 | |
| FR | 3027523 | A1 | * | 4/2016 | A44C 15/002 |
| KR | 20190132368 | A | * | 11/2019 | A44C 25/004 |

* cited by examiner

*Primary Examiner* — Jennifer C Chiang
(74) *Attorney, Agent, or Firm* — Birchwood IP

(57) ABSTRACT

A modular liquid container system includes a bottle main body having a bottle body, a detachable bottle cap, and a detachable dispensing head. Elastic sleeves are fitted onto the bottle body and bottle cap and include integral attachment lugs that provide modular connection interfaces. Ornamental and functional modules may be detachably connected to the attachment lugs by annular buckles. In some embodiments, the modules include scent-diffusing modules formed from magnetically closed half shells having fragrance slots, magnet slots, magnets, and ventilation holes. The system permits interchangeable liquid-dispensing, carrying, decorative, and fragrance-diffusing configurations.

15 Claims, 17 Drawing Sheets

MODULAR LIQUID CONTAINER SYSTEM

TECHNICAL FIELD

The present disclosure relates to the technical field of daily necessities, in particular to a modular liquid container system.

BACKGROUND ART

As a common container for liquid cosmetics, the basic structure of a bottle typically includes a bottle body, a bottle cap and a fixed dispensing head. Existing bottle designs often place emphasis on static aesthetic appeal in appearance, resulting in relatively limited functionality. Against the backdrop of growing user demand for personalization, traditional bottles increasingly reveal issues such as fixed functions, non-customizable decorations, and lack of interactivity and expandability, making it difficult to meet users' composite needs for multifunctionality, customization and portability.

Existing bottle designs often suffer from limited functionality and lack an interchangeable component system; the decorative parts are typically fixed and non-customizable, failing to meet users' personalized needs; the integration between the product and daily items carried by users is low, resulting in insufficient portability and adaptability to various usage scenarios.

Therefore, a modular liquid container system is proposed to address the above issues.

SUMMARY OF THE PRESENT DISCLOSURE

(I) Technical Problems to be Solved

In response to the deficiencies of the prior art, the present disclosure provides a modular liquid container system, which addresses the issues highlighted in the background art, such as fixed functionality and decorations in current bottle designs, lack of interactive modular expandability, and difficulty in meeting users' personalized needs and portability across multiple scenarios.

(II) Technical Solution

The present disclosure adopts the following technical solution to achieve the aforementioned objectives:

- a modular liquid container system, comprising a bottle main body and a functional ornamental component, wherein the bottle main body comprises a bottle body, a bottle cap and a dispensing head, and the dispensing head is installed at the bottle mouth of the bottle body; the functional ornamental component is arranged on the bottle main body.

Further, the bottle mouth of the bottle body is provided with threads; the dispensing head is detachably installed at the bottle mouth of the bottle body and is provided with a ball liquid dispenser or press-type spray nozzle.

Further, the ball liquid dispenser is inserted into the bottle mouth through an interference fit; the press-type spray nozzle is connected to the bottle mouth via the threads.

Further, the bottle cap is a screw cap or plug-in cap adapted to the dispensing head, and the screw cap or the plug-in cap comprises an inner fixed sleeve, an intermediate connecting sleeve and an outer protective shell arranged sequentially from the inside to the outside; the bottle cap is the screw cap screwed to the bottle mouth via the threads when the ball liquid dispenser is installed; the bottle cap is the plug-in cap sleeved to the press-type spray nozzle through the interference fit when the press-type spray nozzle is installed.

Further, the functional ornamental component comprises a bottle body silicone sleeve and a bottle cap silicone sleeve respectively fitted onto the bottle body and the bottle cap, a first attachment lug is arranged on the bottle body silicone sleeve, and a second attachment lug is arranged on the bottle cap silicone sleeve.

Further, at least one U-shaped buckle is sleeved on the second attachment lug and comprises a U-shaped bracket and an L-shaped locking arm, a notch is provided on the U-shaped bracket, the L-shaped locking arm is rotatably arranged inside one end of the U-shaped bracket via a torsion spring pivot shaft, and one end of the L-shaped locking arm extends into the notch.

Further, at least one first annular buckle is sleeved on the second attachment lug, and the second attachment lug is connected to a shell ornament via at least one first annular buckle.

Further, the shell ornament is connected to at least two scent-diffusing modules through at least one second annular buckle; ventilation holes are provided on both sides of the scent-diffusing modules; the scent-diffusing module is composed of two half shells magnetically closed, magnet slots and fragrance slots are provided on the opposing surfaces of the two half shells, magnets are installed inside the magnet slots, and the fragrance slots are designed to contain fragrance.

Further, the two scent-diffusing modules are respectively bear-shaped and heart-shaped; the heart-shaped scent-diffusing module is connected to an ornamental pendant via an iron ring; the first attachment lug is connected to a disc ornament through at least one third annular buckle.

Further, an insertion hole is provided at one end of the first annular buckle, a latch is arranged at the other end thereof via a spring; one end of the latch kept away from the spring extends into the insertion hole; a toggle button is arranged on the latch; the first annular buckle, the second annular buckle and the third annular buckle have the same structure.

(II) Beneficial Effects

Compared with the prior art, the present disclosure provides a modular liquid container system, which offers the following beneficial effects:

The present disclosure achieves interchangeability between the ball liquid dispenser and the press-type spray nozzle through the threaded design of the bottle mouth, enhancing the functional flexibility. The bottle body silicone sleeve and the bottle cap silicone sleeve provide a comfortable non-slip grip. The first attachment lug and the second attachment lug serve as modular interfaces to support function expansion and can be independently replaced for personalized aesthetics. The U-shaped buckle enables quick attachment and detachment to the second attachment lug and allows the bottle to be hung on the external item, improving the portability. The shell ornament, the scent-diffusing module and the disc ornament can be freely combined and connected through the first annular buckle, the second annular buckle and the third annular buckle to form a customizable decorative chain. The scent-diffusing modules also function as fragrance carriers and feature magnetic closure design to facilitate replacement of fragrances. The ventilation holes on both sides ensure fragrance volatilization. The overall design achieves an organic integration of functionality, decoration user experience.

Reference signs: 1. bottle main body; 11. Bottle body; 111. Bottle mouth; 112. Thread; 12. Bottle cap; 121. Screw cap; 122. Plug-in cap; 123. Inner fixed sleeve; 124. Intermediate connecting sleeve; 125. Outer protective shell; 13. Dispensing head; 131. Ball liquid dispenser; 132. Press-type spray nozzle; 2. Scent-diffusing module; 21. Bottle body silicone sleeve; 211. First attachment lug; 22. Bottle cap silicone sleeve; 222. Second attachment lug; 23. U-shaped buckle; 231. U-shaped bracket; 232. L-shaped locking arm; 233. Notch; 234. Torsion spring pivot shaft; 24. First annular buckle; 241. Second annular buckle; 242. Third annular buckle; 243. Insertion hole; 244. Latch; 245. Spring; 246. Toggle button; 25. Shell ornament; 26. Scent-diffusing module; 261. Ventilation hole; 262. Half shell; 263. Magnet slot; 264. Fragrance slot; 265. Magnet; 27. Iron ring; 28. Ornamental pendant; 29. Disc ornament.

DETAILED DESCRIPTION OF THE PRESENT DISCLOSURE

The technical solutions in the embodiments of the present disclosure are clearly and completely described below in conjunction with the drawings. Obviously, the described embodiments represent only part of the embodiments of the present disclosure, but not all of them. All other embodiments obtained by those of ordinary skill in the art based on the embodiments herein without creative efforts shall fall within the scope of protection of the present disclosure.

Embodiments

Figure 1:
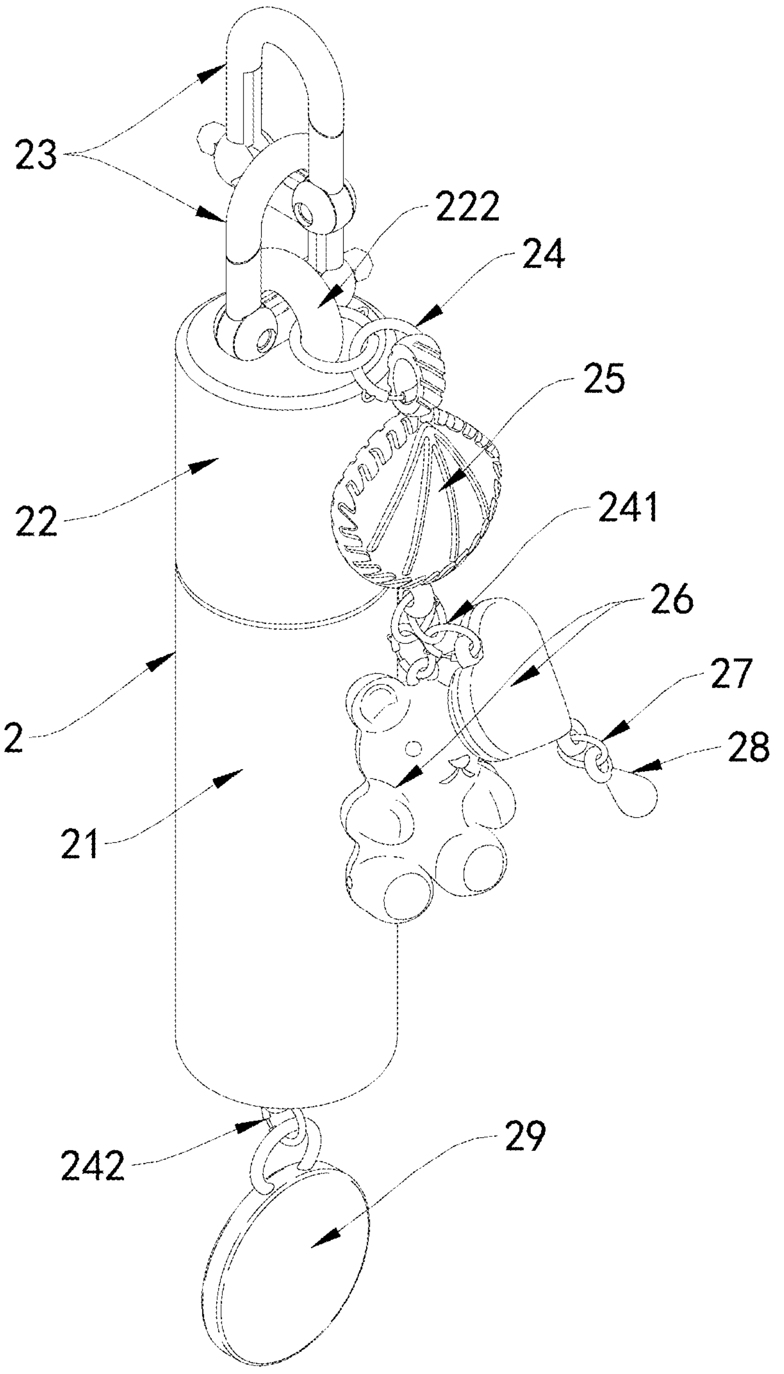
FIG. 1 is a structural diagram of the scent-diffusing module of the present disclosure.
Figure 2:
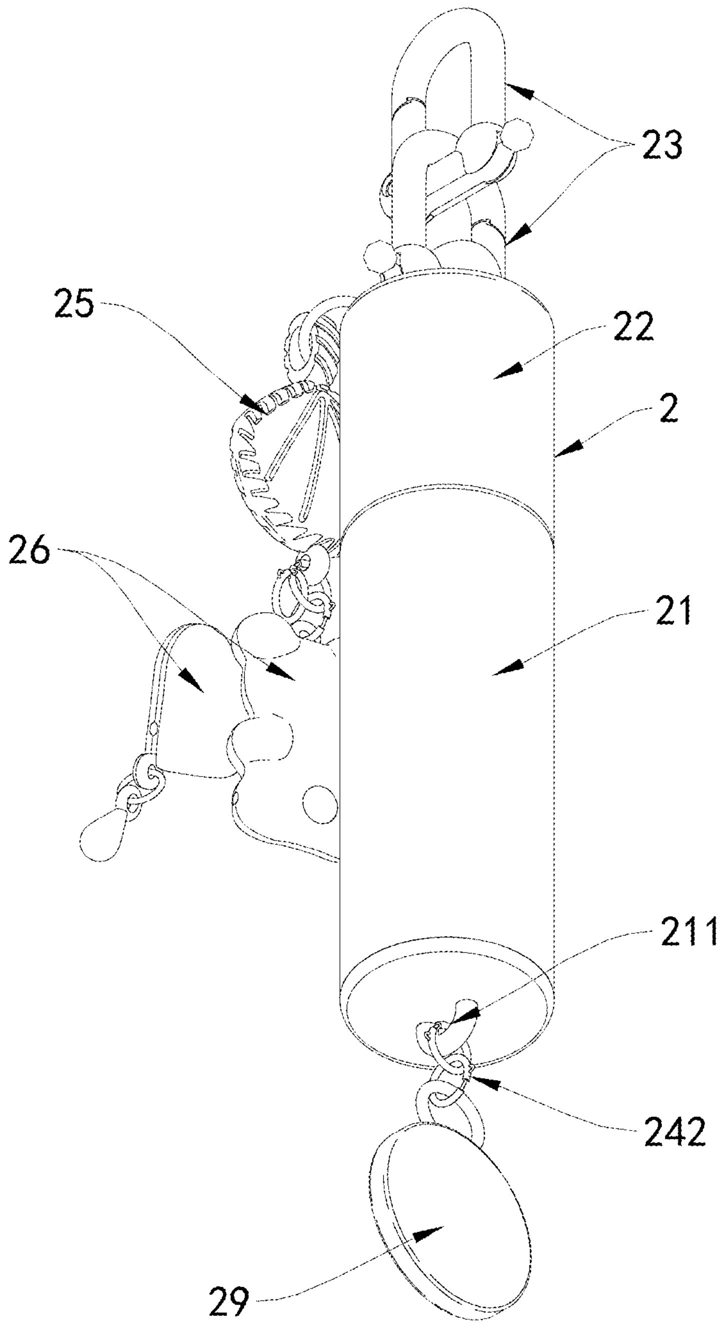
FIG. 2 is a structural diagram of the scent-diffusing module of the present disclosure.
Figure 3:
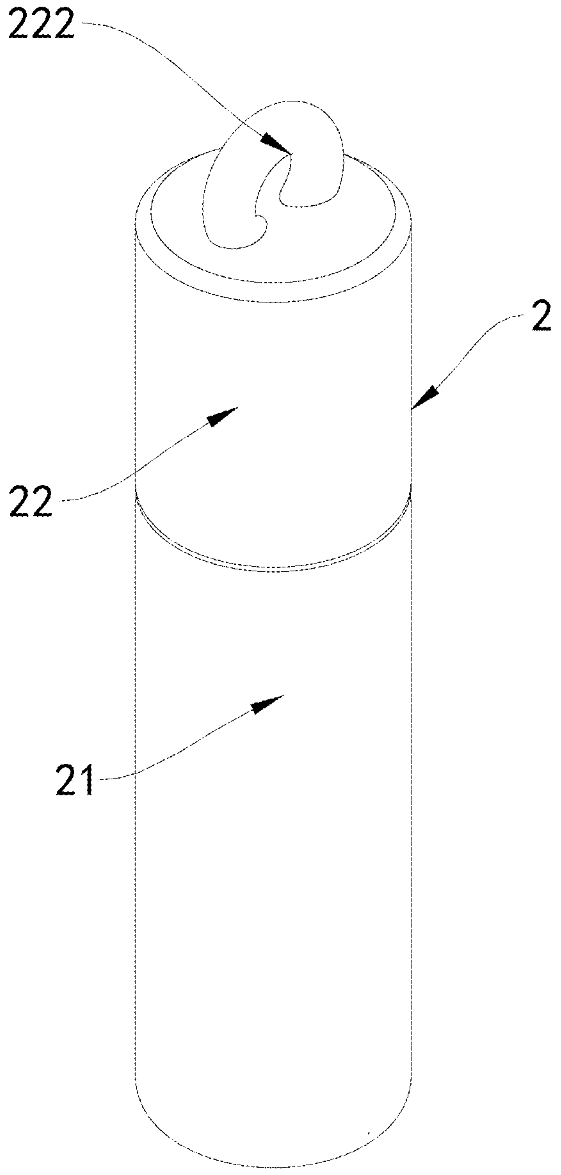
FIG. 3 is a structural diagram of the bottle body silicone sleeve and bottle cap silicone sleeve of the present disclosure.
Figure 4:
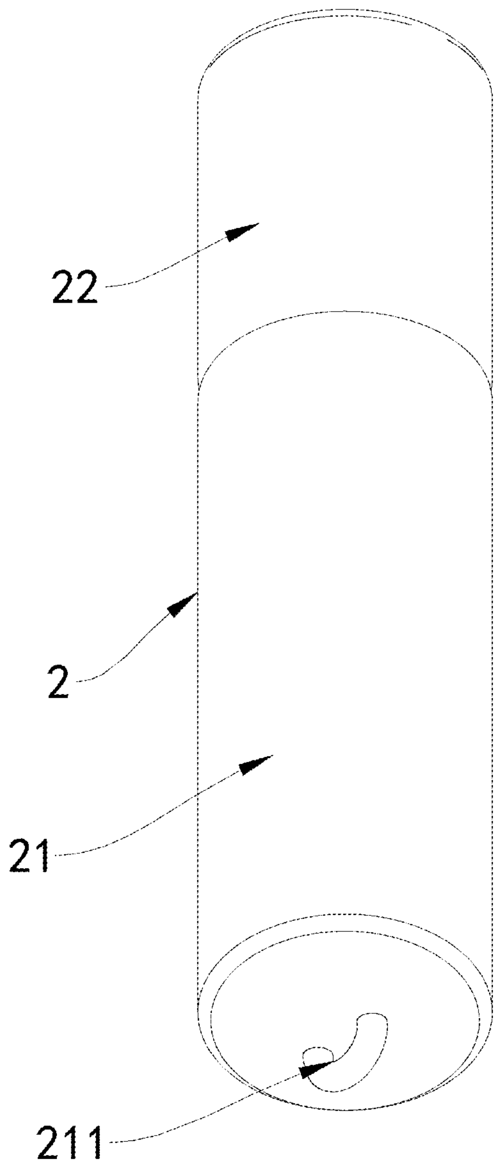
FIG. 4 is a structural diagram of the bottle body silicone sleeve and bottle cap silicone sleeve of the present disclosure.
Figure 5:
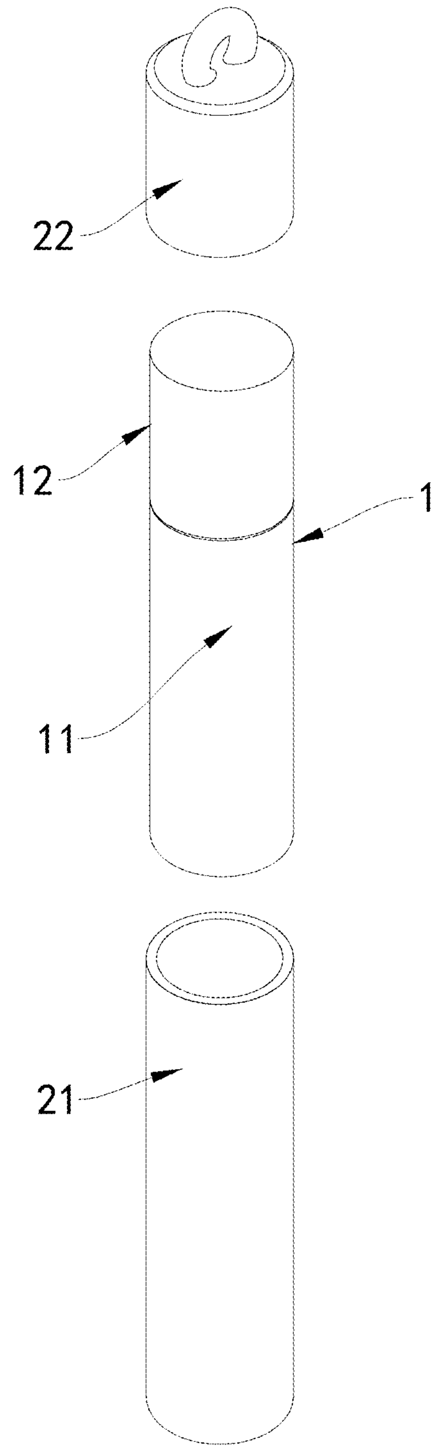
FIG. 5 is a structural diagram of the bottle main body of the present disclosure.
Figure 6:
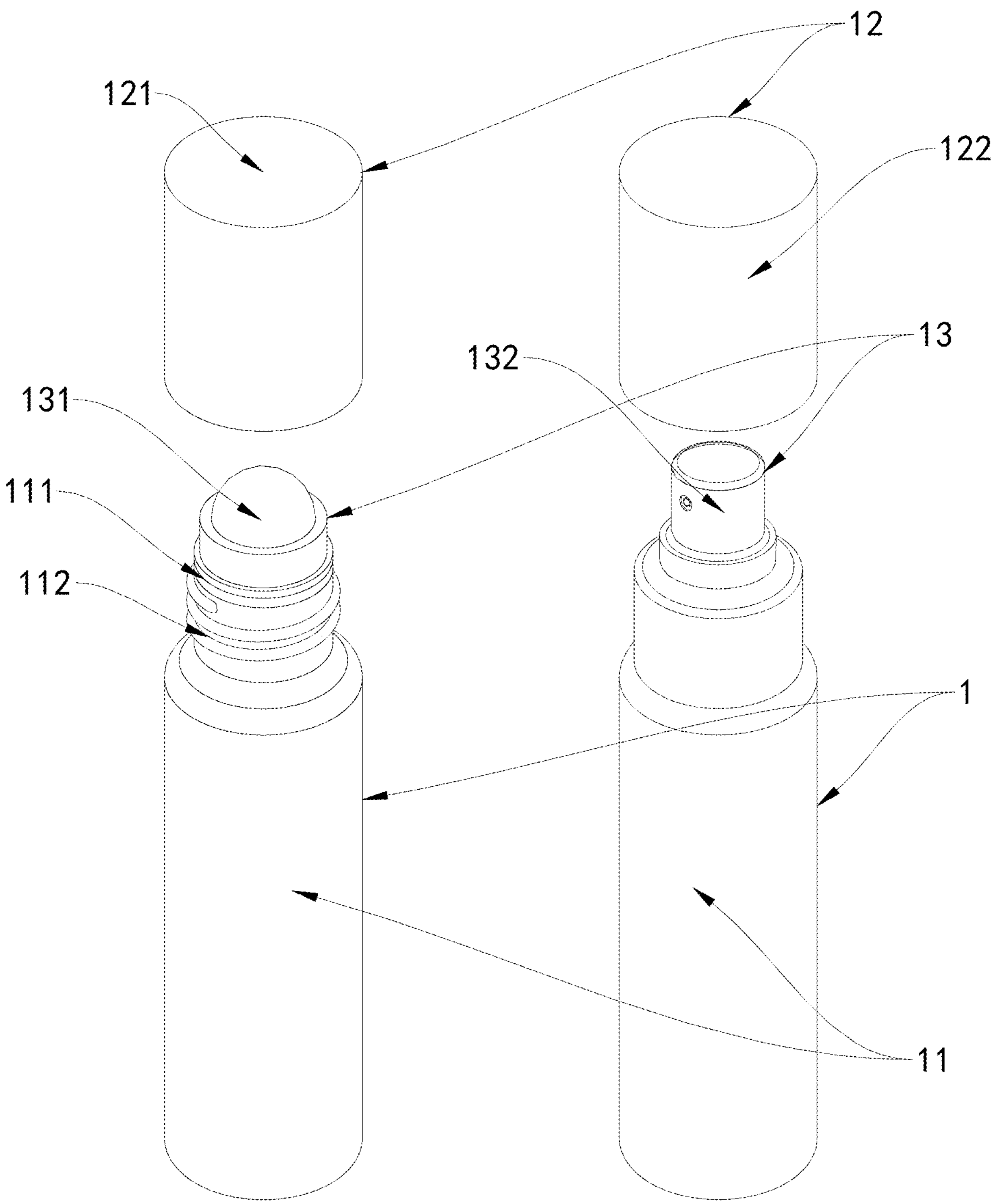
FIG. 6 is a structural diagram of the dispensing head of the present disclosure.
Figure 7:
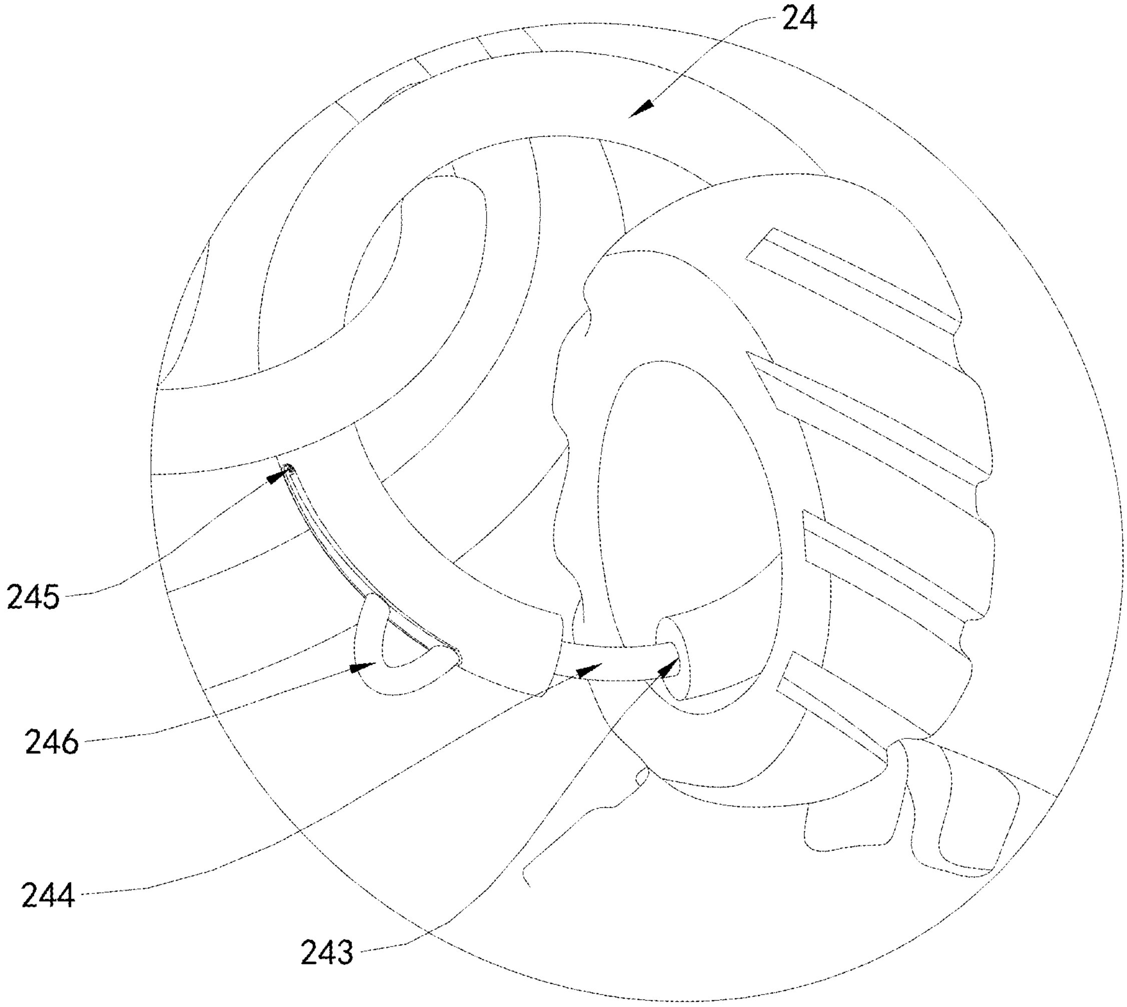
FIG. 7 is a structural diagram of the first annular buckle of the present disclosure.
Figure 8:
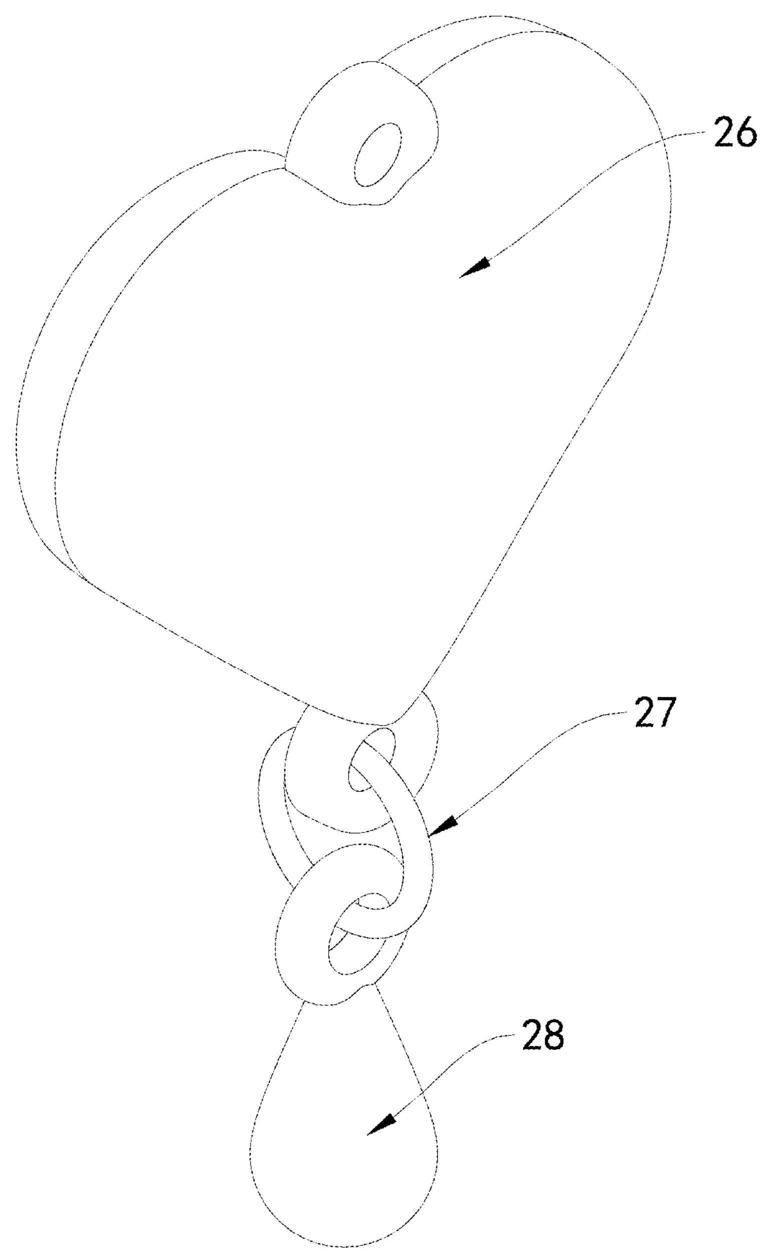
FIG. 8 is a structural diagram of the heart-shaped scent-diffusing module of the present disclosure.
Figure 9:
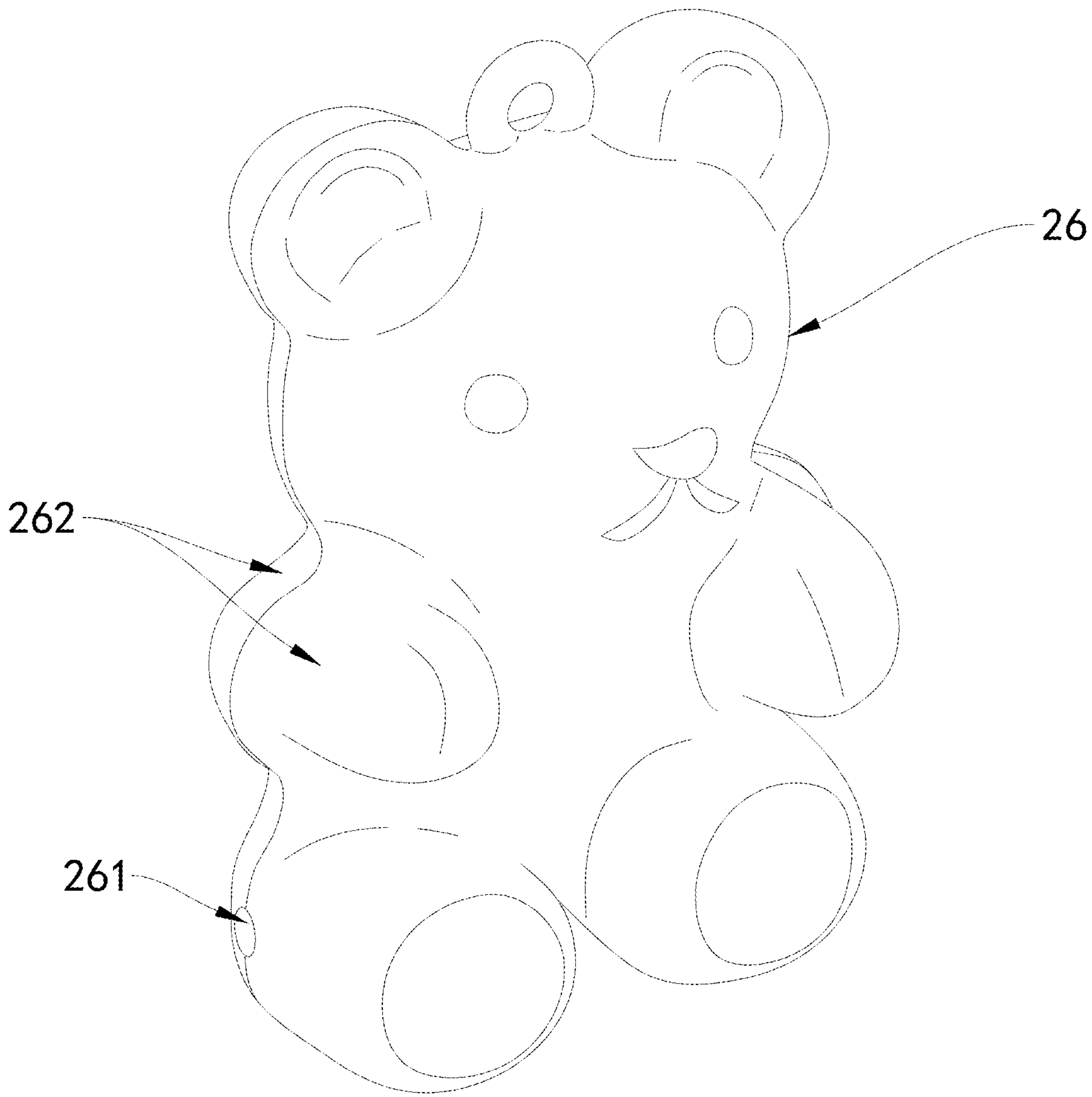
FIG. 9 is a structural diagram of the bear-shaped scent-diffusing module of the present disclosure.
Figure 10:
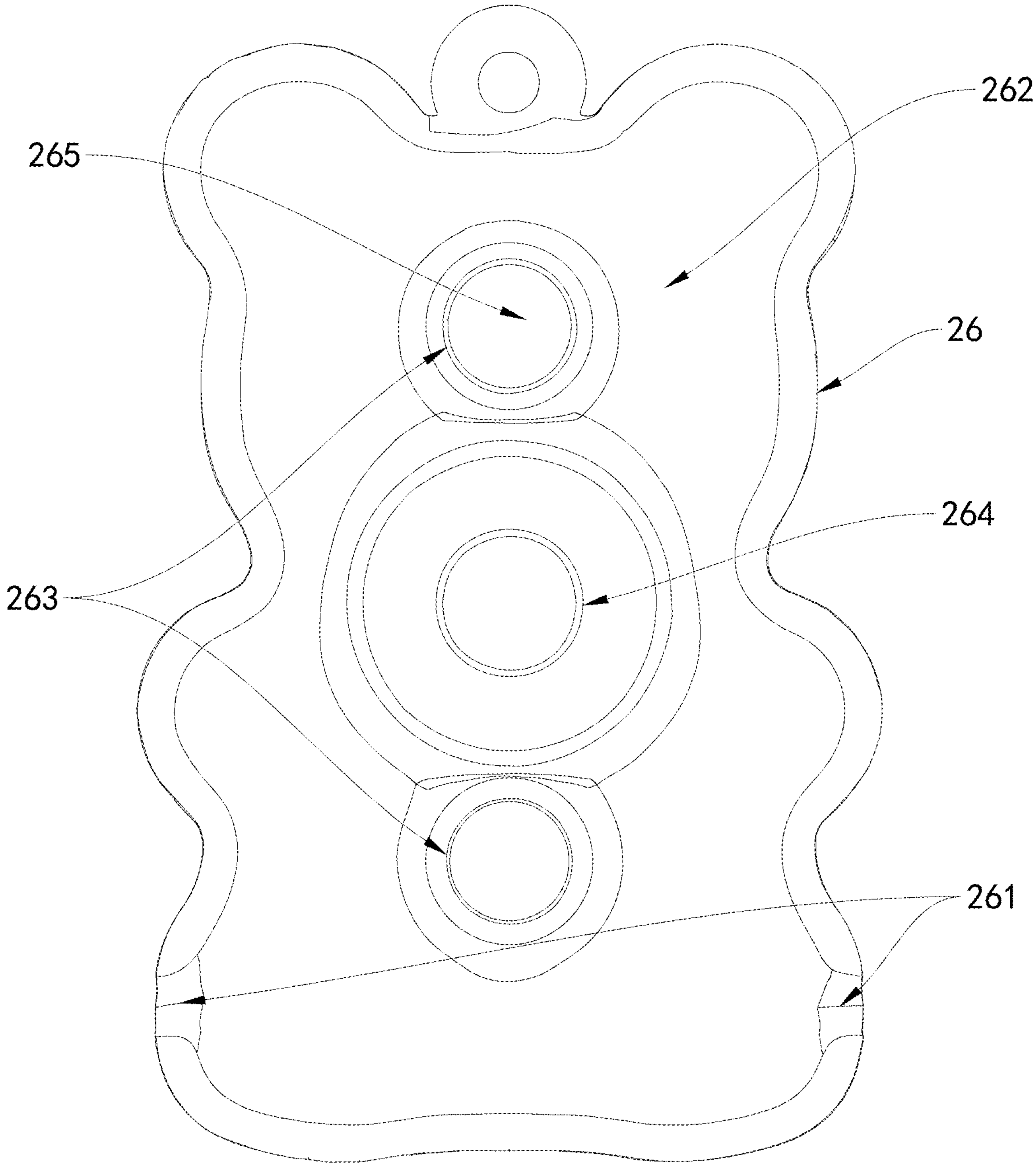
FIG. 10 is a cross-sectional view of the bear-shaped scent-diffusing module of the present disclosure.
Figure 11:
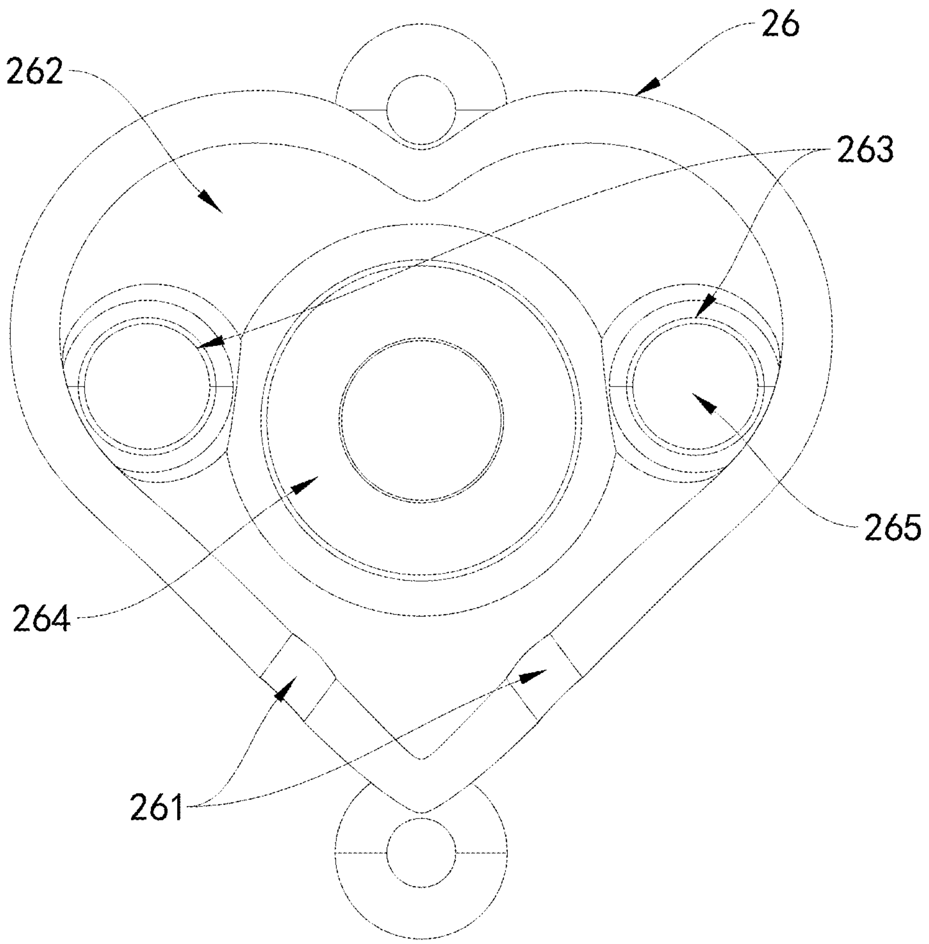
FIG. 11 is a cross-sectional view of the heart-shaped scent-diffusing module of the present disclosure.
Figure 12:
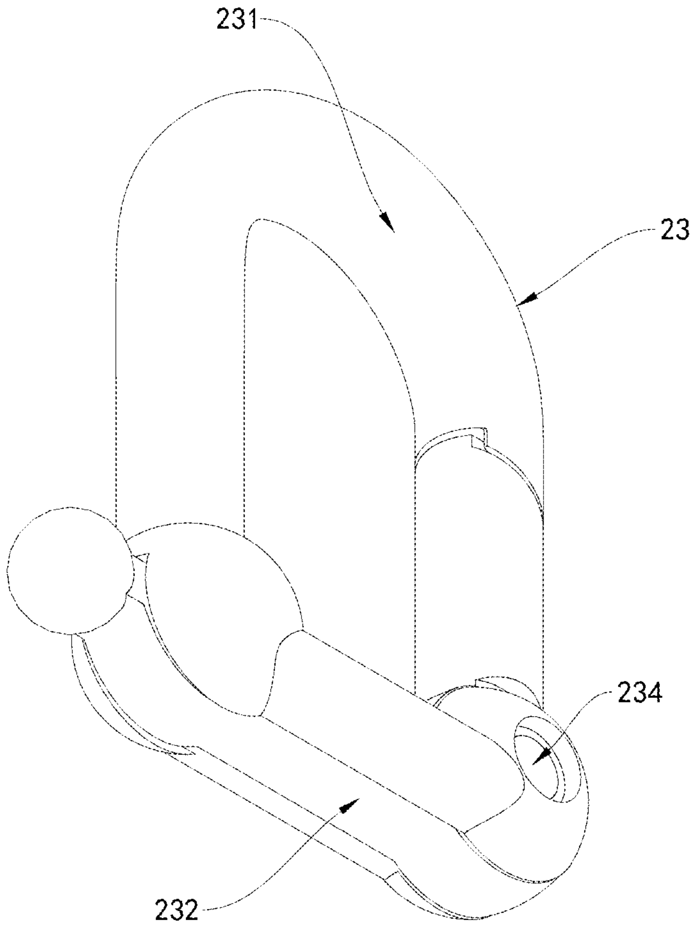
FIG. 12 is a structural diagram of the U-shaped buckle of the present disclosure.
Figure 13:
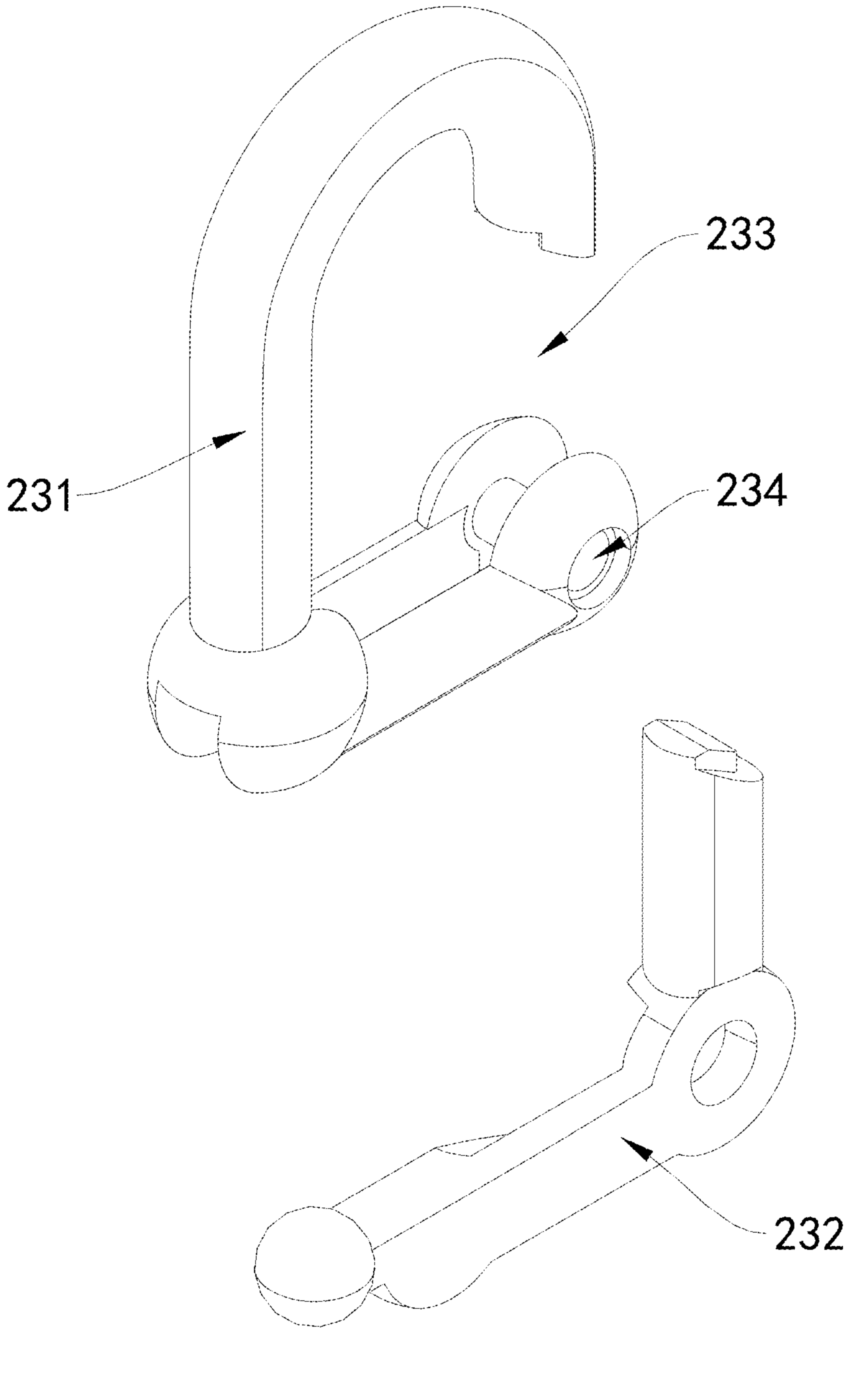
FIG. 13 is an exploded view of the U-shaped buckle of the present disclosure.
Figure 14:
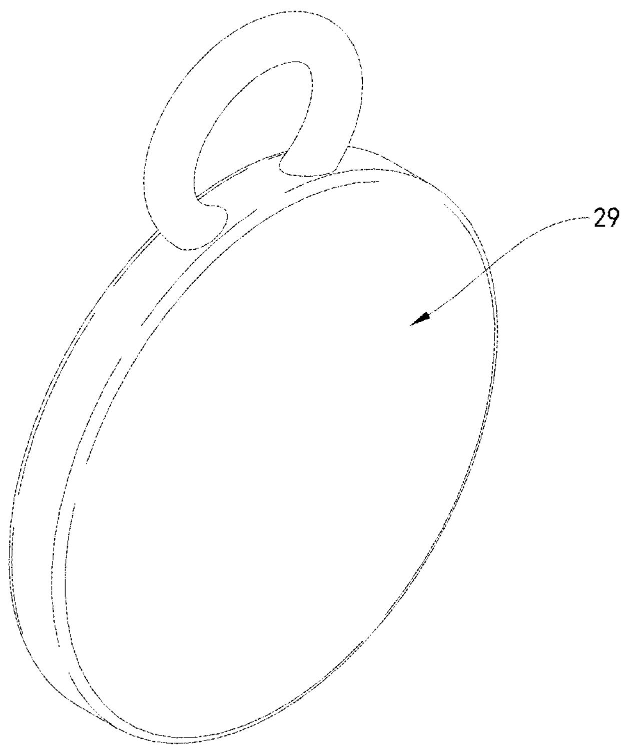
FIG. 14 is a structural diagram of the disc ornament of the present disclosure.
Figure 15:
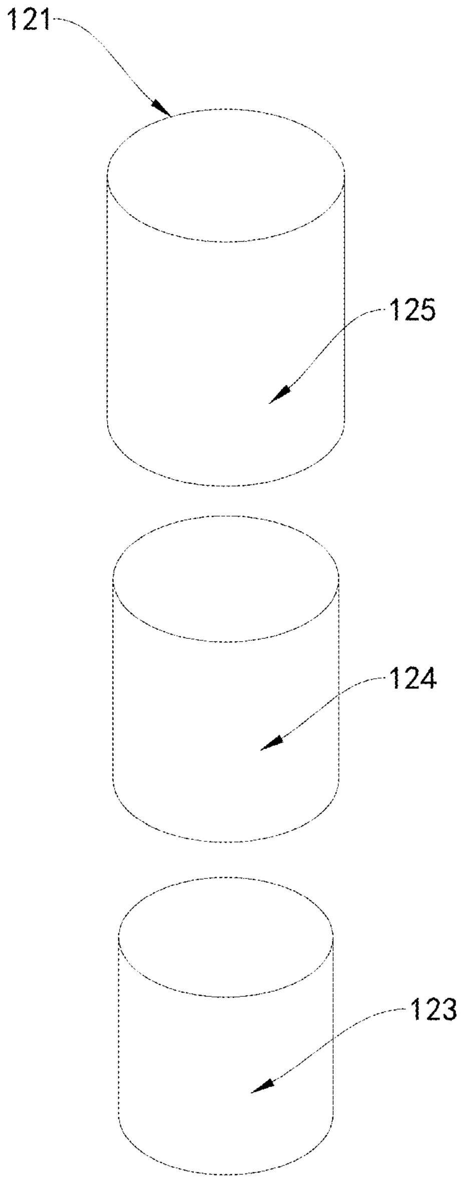
FIG. 15 is an exploded view of the screw cap of the present disclosure.
Figure 16:
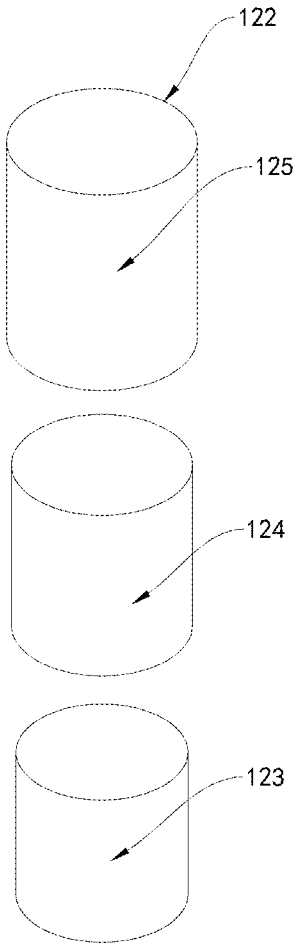
FIG. 16 is an exploded view of the plug-in cap of the present disclosure.
Figure 17:
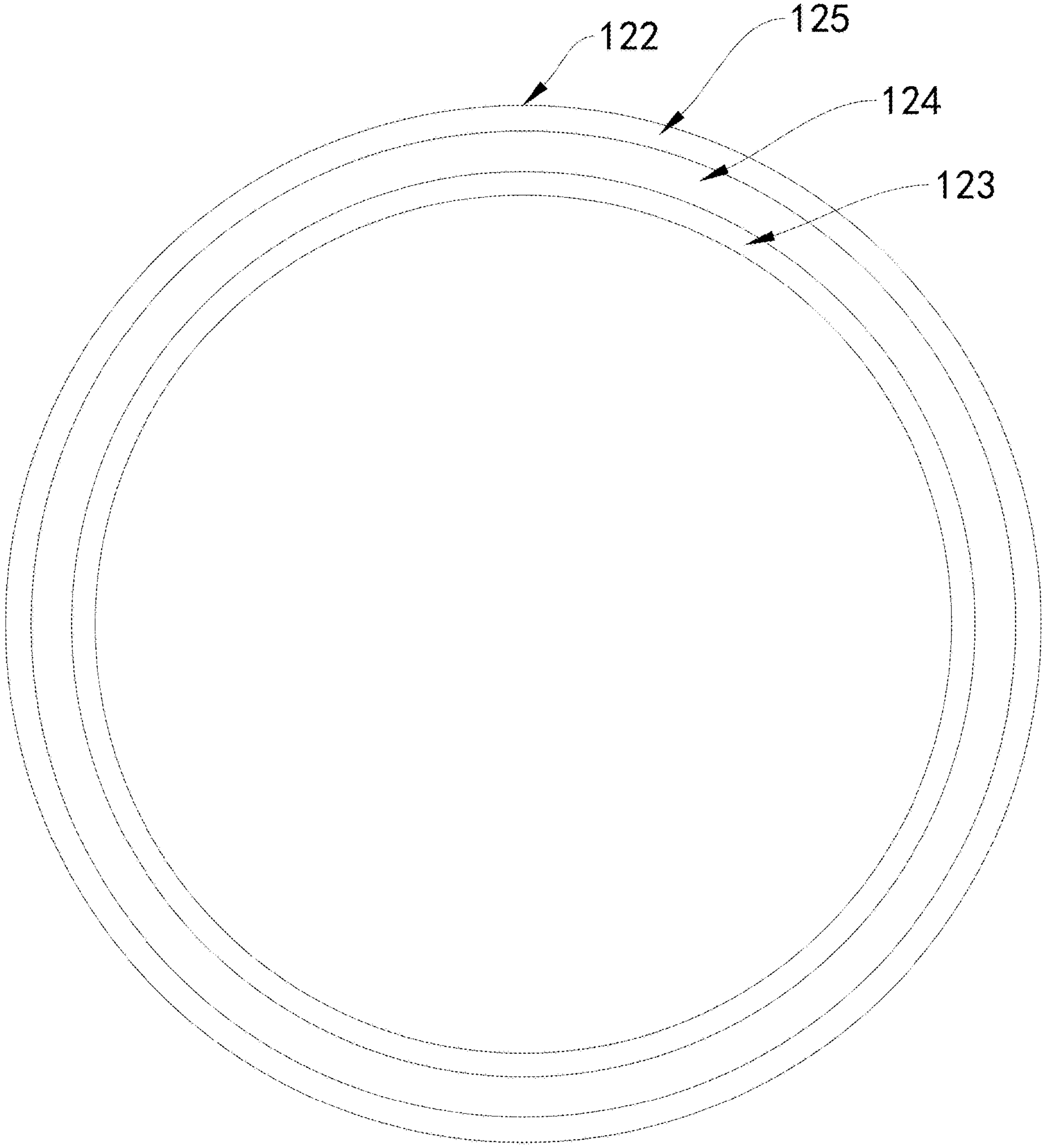
FIG. 17 is a cross-sectional view of the plug-in cap of the present disclosure.

As shown in FIGS. 1-17, one embodiment of the present disclosure proposes a modular liquid container system, comprising a bottle main body 1 and a functional ornamental component 2, wherein the bottle main body 1 comprises a bottle body 11, a bottle cap 12 and a dispensing head 13, and the dispensing head 13 is installed at the bottle mouth 111 of the bottle body 11; the functional ornamental component 2 is arranged on the bottle main body 1.

As shown in FIGS. 1-17, in some embodiments, the bottle mouth 111 of the bottle body 11 is provided with threads 112; the dispensing head 13 is detachably installed at the bottle mouth 111 of the bottle body 11 and is provided with a ball liquid dispenser 131 or press-type spray nozzle 132.

The bottle mouth 111 is standardized as a thread 112 interface, achieving the interchangeability and systematization of core functional modules. Users can freely choose and interchange between the ball liquid dispenser 131 and the press-type spray nozzle 132 based on different usage scenarios (such as precise application or quick spraying) and the characteristics of the perfume, significantly enhancing the functional flexibility and user experience of a single bottle. The standardized thread 112 design also facilitates the universal production and assembly of components.

As shown in FIGS. 1-17, in some embodiments, the ball liquid dispenser 131 is inserted into the bottle mouth 111 through an interference fit; the press-type spray nozzle 132 is connected to the bottle mouth 111 via the threads 112.

The ball liquid dispenser 131 is pressed into the bottle mouth 111 through interference fit by utilizing the elastic deformation of the plastic part. This achieves convenient assembly and disassembly and enables an effective seal to be formed by means of tight compression between materials, preventing liquid leakage or volatilization the press-type spray nozzle 132 achieves secure mechanical fixation through the thread 112 connection, ensuring that the structure remains tight under repeated pressing operations and can withstand internal liquid pressure, thereby guaranteeing reliable sealing.

As shown in FIGS. 1-17, in some embodiments, the bottle cap 12 is a screw cap 121 or plug-in cap 122 adapted to the dispensing head 13, and the screw cap 121 or plug-in cap 122 comprises an inner fixed sleeve 123, an intermediate connecting sleeve 124 and an outer protective shell 125 arranged sequentially from the inside to the outside; the bottle cap 12 is the screw cap 121 screwed to the bottle mouth 111 via the threads 112 when the ball liquid dispenser 131 is installed; the bottle cap 12 is the plug-in cap 122 sleeved to the press-type spray nozzle 132 through the interference fit when the press-type spray nozzle 132 is installed.

For the ball liquid dispenser 131, the screw cap 121 and the bottle mouth 111 adopts thread 112 fit to provide strong and uniform pressing force, ensuring long-term sealing and preventing perfume volatilization. For the press-type spray nozzle 132 with a protruding pressing head, the plug-in cap 122 is used. The plastic plug-in cap 122 is directly sleeved onto the spray nozzle through the interference fit by utilizing the elasticity of the main body of the plastic plug-in cap 122, enabling quick opening and closing with exceptional convenience while delivering the effects of effective dust prevention, false touch rejection and sealing. The plug-in cap 122 balances both sealing performance and ease of use.

Both the screw cap 121 and the plug-in cap 122 adopt a three-layer composite structure, comprising the inner fixed sleeve 123, the intermediate connecting sleeve 124 and the outer protective shell 125. The inner fixed sleeve 123 serves as a core functional layer, which achieves sealing through the threads 112 in the screw cap 121, provides fixation in the plug-in cap 122 through the interference fit, and ensures reliable sealing and connection strength. The intermediate connecting sleeve 124 acts as a structural reinforcement layer, securely connecting the inner and outer layers, effectively enhancing the overall rigidity of the cap body and distributing stress to prevent deformation. The outer protective shell 125 functions as an appearance layer, offering ample space for aesthetic design and surface protection. This composite process achieves optimal material utilization through functional layering (e.g., the inner layer lays emphasis on strength and corrosion resistance, while the outer layer places emphasis on texture and color), reduces the overall manufacturing difficulty and costs of complex structures, and allows for personalized appearance by replacing the outer protective shell 125, thereby significantly improving product reliability, manufacturing economy, and user experience.

As shown in FIGS. 1-17, in some embodiments, the functional ornamental component 2 comprises a bottle body silicone sleeve 21 and a bottle cap silicone sleeve 22 respectively fitted onto the bottle body 11 and the bottle cap 12, a first attachment lug 211 is arranged on the bottle body silicone sleeve 21, and a second attachment lug 222 is arranged on the bottle cap silicone sleeve 22.

The bottle body silicone sleeve 21 and the bottle cap silicone sleeve 22 fundamentally enhance the gripping experience and functional expandability of the product. The silicone material provides a soft, comfortable hand feel and excellent slip resistance, ensuring that the user holds more securely and comfortably. The first attachment lug 211 and the second attachment lug 222 are integrally molded onto the bottle body silicone sleeve 21 and the bottle cap silicone sleeve 22 and serve as sturdy anchor points, providing modular interfaces for subsequently hanging or connecting various decorative or functional parts, and achieving a foundational integration of aesthetics and functionality.

The bottle body silicone sleeve 21 and the bottle cap silicone sleeve 22 can be independently detached and replaced from the bottle main body 1. Users can match the bottle body silicone sleeve 21 and bottle cap silicone sleeve 22 in different colors according to personal preferences, seasons or occasions, achieving a high degree of appearance personalization and fashion matching freedom, allowing for low-cost replacement when the bottle body silicone sleeve 21 or bottle cap silicone sleeve 22 becomes worn or soiled, and enhancing the economic value and sustainability of the product.

As shown in FIGS. 1-17, in some embodiments, at least one U-shaped buckle 23 is sleeved on the second attachment lug 222 and comprises a U-shaped bracket 231 and an L-shaped locking arm 232, a notch 233 is provided on the U-shaped bracket 231, the L-shaped locking arm 232 is rotatably arranged inside one end of the U-shaped bracket 231 via a torsion spring pivot shaft 234, and one end of the L-shaped locking arm 232 extends into the notch 233.

The U-shaped buckle 23 is ingeniously designed as a quick-release connecting mechanism. When the open end of the U-shaped bracket 231 is pressed toward the second attachment lug 222, the second attachment lug 222 pushes against the extended end of the L-shaped locking arm 232, causing the L-shaped locking arm 232 to rotate and open against the torque of the torsion spring pivot shaft 234 and enter the U-shaped bracket 231. Alternatively, the notch 233 can be manually opened to sleeve the second attachment lug 222 by pulling the end of the L-shaped locking arm 232 kept away from the notch 233; subsequently, under the rebound effect of the torsion spring pivot shaft 234, the L-shaped locking arm 232 returns to its original position, with its end clamped into and sealing the notch 233 to block the second attachment lug 222, achieving self-locking. the notch 233 can be opened by pulling one end of the L-shaped locking arm 232 kept away from the notch 233 or directly pressing the portion of the L-shaped locking arm 232 corresponding to the notch 233, thereby allowing the second attachment lug 222 to disengage through the notch 233 and releasing locking. This structure eliminates the need of threading in traditional rings, enabling one-button quick installation and removal of decorative chains.

The U-shaped buckle 23 serves as a quick connection point for decorative chains. Additionally, due to standardized interface properties and reliable mechanical locking capability, the U-shaped buckle 23 functions as a universal external hanging hub connecting the entire modular liquid container system to the user's personal item. Specifically, the user can quickly buckle the open end of the U-shaped bracket 231 for the U-shaped buckle 23 onto external anchor points such as string ring on the backpack, key ring, belt loop or D-ring on the handbag, enabling hands-free portable hanging of the bottle. This design significantly expands the product's usage scenarios: the bottle main body 1 can be securely hung on the exterior of the backpack for easy access, or serve as serve as a fashion pendant attached to the key or bag, combining functionality with decorative appeal. By cleverly leveraging the inherent "intermediary" nature of the U-shaped buckle 23, the bottle main body 1 requires no structural alterations. Specifically, through the fit between the second attachment lug 222 and the U-shaped buckle 23, an item stored in the bag or placed on the table is seamlessly transitioned into a dynamic fashion accessory that can be carried closely at all times, is less prone to loss and offers convenient access. This comprehensively enhances the product's portability, accessibility and adaptability for outdoor use.

As shown in FIGS. 1-17, in some embodiments, at least one first annular buckle 24 is sleeved on the second attachment lug 222, and the second attachment lug 222 is connected to a shell ornament 25 via at least one first annular buckle 24.

The first annular buckle 24 serves as a standard chain link unit, characterized by simple structure, low cost, and flexible connectivity. Users can interlink a plurality of first annular buckles 24 in series to easily form a chain link of the desired length. One end of the chain link is then sleeved to the second attachment lug 222, and the other end thereof is connected to the shell ornament 25. This design allows users to freely adjust the initial hanging height of ornaments according to personal preferences, achieving personalized ornament customization.

As shown in FIGS. 1-17, in some embodiments, the shell ornament 25 is connected to at least two scent-diffusing modules 26 through at least one second annular buckle 241; ventilation holes 261 are provided on both sides of the scent-diffusing modules 26; the scent-diffusing module 26 is composed of two half shells 262 magnetically closed, magnet slots 263 and fragrance slots 264 are provided on the opposing surfaces of the two half shells 262, magnets 265 are installed inside the magnet slots 263, and the fragrance slots 264 are designed to contain fragrance.

The scent-diffusing modules 26 simultaneously function as the fragrance carriers, enabling the modular liquid container system to emit dual or varying scents, and delivering an excellent user experience. Through the magnetic closure design, users can effortlessly separate or combine the two half shells 262 by hands without any tools, facilitating the replacement of fragrances. The ventilation holes 261 on both sides ensure air circulation, allowing the fragrances placed in the fragrance slots 264 to volatilize scent continuously and evenly. The connection mode via the second annular buckle 241 maintains the modular expandability of the decorative chain, allowing users to freely increase and decrease the quantity of the scent-diffusing modules 26 or adjust the sequence of the scent-diffusing modules 26.

As shown in FIGS. 1-17, in some embodiments, the two scent-diffusing modules 26 are respectively bear-shaped and heart-shaped; the heart-shaped scent-diffusing module 26 is connected to an ornamental pendant 28 via an iron ring 27; the first attachment lug 211 is connected to a disc ornament 29 through at least one third annular buckle 242.

The bear-shaped and heart-shaped scent-diffusing modules 26 endow the product with adorable and heartwarming emotional value. The decorative pendant 28 is connected via the iron ring 27, adding a sense of vitality below the main decorative chain and enhancing the visual layering. On the first attachment lug 211 positioned on the side of the bottle body 11, the disc ornament 29 is connected through the third annular buckle 242, breaking the sense of imbalance of focusing decorative elements solely on the side of the bottle cap 12, creating a visual harmony between the left and right sides of the modular liquid container system, achieving balanced composition, and elevating the overall sense of design.

The core advantages of the scent-diffusing modules 26 lie in highly customizable form and universal flexibility of connection methods. The specific shapes of the ornaments are not limited to the examples of a bear or a heart; the design principle can be extended to any three-dimensional or flat shape favored by users (such as star, flower, geometric pattern, letter, etc.), thereby meeting the personalized aesthetic needs of different user groups and transforming the product into an emotional carrier for expressing individual style. Regarding the connection methods, the iron ring 27 serves as a connecting piece that provides flexible swinging movement and can be replaced with one or more first annular buckles 24 connected end to end based on design requirements, forming a chain link with adjustable length or in specific shape. This interchangeability of connecting pieces ensures that the entire decorative chain system is not only freely combined in visual elements but also highly modular and reconfigurable in physical connection structure. Users can freely select decorative pieces of different styles just like matching jewelry, and connect them in series, parallel, or branched combinations using standardized connectors such as the U-shaped buckles 23 and the first annular buckles 24, creating unique hanging decorative effects. This design transforms the bottle from a mere container into a personalized fashion accessory that users can deeply customize, significantly enhancing the product's appeal, interactivity, and added value.

As shown in FIGS. 1-17, in some embodiments, an insertion hole 243 is provided at one end of the first annular buckle 24, a latch 244 is arranged at the other end thereof via a spring 245; one end of the latch 244 kept away from the spring 245 extends into the insertion hole 243; a toggle button 246 is arranged on the latch 244; the first annular buckle 24, the second annular buckle 241 and the third annular buckle 242 have the same structure.

When it is necessary to connect two annular buckles (the first annular buckle 24, the second annular buckle 241, or the third annular buckle 242) or to connect the annular buckle to the lug portion of the ornament (the shell ornament 25, the scent-diffusing module 26 or the disc ornament 29), the toggle button 246 is pressed to retract the latch 244 against the force of the spring 245, thereby exposing the opening between the two ends of the annular buckle. Through the opening, another annular buckle (the first annular buckle 24, the second annular buckle 241, or the third annular buckle 242) or the lug portion of the ornament (the shell ornament 25, the scent-diffusing module 26 or the disc ornament 29) or the first attachment lug 211 or the second attachment lug 222 can be sleeved. The toggle button 246 is released to allow the latch 244 to be automatically inserted into the insertion hole 243 under the rebound effect of the spring 245, closing the opening, achieving automatic locking and preventing detachment. This structure ensures that decorative chain formed by connecting a plurality of annular buckles (the first annular buckle 24, the second annular buckle 241, or the third annular buckle 242) in series remain secure and reliable during use, and enables rapid assembly and disassembly of chain links through a simple pressing operation, granting users the greatest DIY freedom. All annular buckles (the first annular buckle 24, the second annular buckle 241, and the third annular buckle 242) have the same structure, significantly simplifying production and accessories management.

To sum up, a high degree of customization in both functionality and decoration of the bottle is achieved through modular design. The dispensing head 13 is designed as the interchangeable ball liquid dispenser 131 or press-type spray nozzle 132, and bottle mouth 111 is provided with the threads 112, so that users can freely switch between precise application and quick spraying modes based on usage scenarios, significantly expanding the applicability of a single product. The matched screw cap 121 and plug-in cap 122 are respectively screwed and sleeved through the threads 112 and the interference fit, and provide reliable and convenient sealing solutions for different dispensing heads 13, ensuring both the stability of perfume storage and the ease of access.

The independently replaceable bottle body silicone sleeve 21 and bottle cap silicone sleeve 22 offer comfortable gripping hand feel and slip resistance; the first attachment lug 211 and the second attachment lug 222 integrally molded on the bottle body silicone sleeve 21 and the bottle cap silicone sleeve 22 form a standardized functional expansion interface. The U-shaped buckle 23 sleeved onto the second attachment lug 222 utilizes the ingenious structure of L-shaped locking arm 232 and torsion spring pivot shaft 234 to achieve one-button quick-release connection with decorative chains or external hanging rings, significantly enhancing hanging portability and usage flexibility, and allowing the bottle to be easily transformed into a portable accessory.

Furthermore, the connection system composed of the first annular buckle 24, the second annular buckle 241 and the third annular buckle 242 connected in series is combined with diversified ornaments such as the shell ornament 25, the bear-shaped scent-diffusing module 26 and the heart-shaped scent-diffusing module 26, forming a highly customizable decorative chain. Particularly, the scent-diffusing modules 26 adopt the structures of the half shells 262 magnetically closed, inside which the fragrance slots 264 and the ventilation holes 261 are provided, allowing the scent-diffusing modules 26 to offer the practical function of continuously diffuse fragrance. This design integrates decoration, enjoyment, personalized customization and functional expansion, comprehensively enhancing the product's user experience and market competitiveness.

Finally, it should be noted that the above descriptions are merely preferred embodiments of the present disclosure and are not intended to limit the present disclosure. Although the present disclosure has been described in detail with reference to the aforementioned embodiments, those skilled in the art may still modify the technical solutions recorded in the aforementioned embodiments or equivalently replace some of the technical features therein. Any modifications, equivalent substitutions, improvements, etc., made within the spirit and principles of the present disclosure shall fall within the protection scope of the present disclosure.

The invention claimed is:

1. A modular liquid container system, comprising:

a bottle main body comprising a bottle body having a bottle mouth and a detachable bottle cap;

a dispensing head detachably installed at the bottle mouth;

a bottle body elastic sleeve fitted onto an exterior of the bottle body, the bottle body elastic sleeve comprising an integral first attachment lug extending outwardly therefrom;

a bottle cap elastic sleeve fitted onto an exterior of the detachable bottle cap, the bottle cap elastic sleeve comprising an integral second attachment lug extending outwardly therefrom; and a modular functional ornamental component detachably connected to at least one of the first attachment lug and the second attachment lug, wherein the modular functional ornamental component comprises a shell ornament connected to the second attachment lug via at least one first annular buckle and at least two scent-diffusing modules connected to the shell ornament via at least one second annular buckle, and wherein each scent-diffusing module comprises two half shells magnetically closed together, magnet slots and fragrance slots provided on opposing surfaces of the two half shells, magnets installed in the magnet slots, and ventilation holes provided on both sides of the scent-diffusing module.

2. The modular liquid container system according to claim 1, wherein the bottle mouth of the bottle body is provided with thread; the dispensing head is detachably installed at the bottle mouth of the bottle body.

3. The modular liquid container system according to claim 2, wherein the dispensing head is provided with a ball liquid dispenser.

4. The modular liquid container system according to claim 2, wherein the dispensing head is provided with a press-type spray nozzle.

5. The modular liquid container system according to claim 3, wherein the ball liquid dispenser is inserted into the bottle mouth through an interference fit.

6. The modular liquid container system according to claim 4, wherein the press-type spray nozzle is connected to the bottle mouth via the threads.

7. The modular liquid container system according to claim 1, wherein the bottle cap comprises a plurality of functional layers, including an inner structure for fixation and an outer structure for external protection or decoration.

8. The modular liquid container system according to claim 7, wherein the bottle cap is the screw cap screwed to the bottle mouth via the threads when the ball liquid dispenser is installed.

9. The modular liquid container system according to claim 7, wherein the bottle cap is the plug-in cap sleeved to the press-type spray nozzle through the interference fit when the press-type spray nozzle is installed.

10. The modular liquid container system according to claim 1, wherein the bottle body elastic sleeve and the bottle cap elastic sleeve comprise silicone.

11. The modular liquid container system according to claim 1, wherein at least one buckle is sleeved on the second attachment lug and comprises a bracket and a locking arm, and a notch is provided on the bracket.

12. The modular liquid container system according to claim 11, wherein the locking arm is rotatably arranged inside one end of the bracket via a torsion spring pivot shaft, and one end of the locking arm extends into the notch.

13. The modular liquid container system according to claim 1, wherein the at least two scent-diffusing modules comprise ornamental bodies of predetermined shapes; at least one of the scent-diffusing modules is connected to an ornamental pendant via a linking ring; and the first attachment lug is connected to an ornamental body through at least one third annular buckle.

14. The modular liquid container system according to claim 13, wherein an insertion hole is provided at one end of the first annular buckle, a latch is arranged at the other end thereof via a spring; one end of the latch kept away from the spring extends into the insertion hole; a toggle button is arranged on the latch; the first annular buckle, the second annular buckle and the third annular buckle have the same structure.

15. A modular functional ornamental component configured for detachable connection to an attachment lug of an elastic sleeve fitted onto a liquid container, comprising:

a shell ornament;

at least two scent-diffusing modules, wherein each scent-diffusing module is composed of two half shells magnetically closed, magnet slots and fragrance slots are provided on the opposing surfaces of the two half shells, magnets are installed inside the magnet slots, and the fragrance slots are designed to contain fragrance; ventilation holes are provided on both sides of the scent-diffusing module;

at least one annular buckle detachably connecting the at least two scent-diffusing modules to the shell ornament, wherein an insertion hole is provided at one end of the annular buckle, a latch is arranged at another end of the annular buckle via a spring, one end of the latch extends into the insertion hole, and a toggle button is arranged on the latch.

* * * * *